United States Patent
Baker et al.

(10) Patent No.: US 11,911,412 B2
(45) Date of Patent: *Feb. 27, 2024

(54) DERIVATIZED CHITOSAN POLYMERS AND METHODS OF TREATING VASCULAR DISORDERS

(71) Applicant: SYNEDGEN, INC., Claremont, CA (US)

(72) Inventors: Shenda M. Baker, Upland, CA (US); William P. Wiesmann, Chevy Chase, MD (US)

(73) Assignee: SYNEDGEN, INC., Claremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/362,254

(22) Filed: Jun. 29, 2021

(65) Prior Publication Data

US 2022/0160754 A1 May 26, 2022

Related U.S. Application Data

(63) Continuation of application No. 15/752,852, filed as application No. PCT/US2016/046829 on Aug. 12, 2016, now Pat. No. 11,077,135.

(60) Provisional application No. 62/205,408, filed on Aug. 14, 2015.

(51) Int. Cl.
| | |
|---|---|
| *A61K 31/726* | (2006.01) |
| *A61K 9/00* | (2006.01) |
| *A61K 31/7008* | (2006.01) |
| *A61K 31/715* | (2006.01) |
| *A61K 45/06* | (2006.01) |
| *A61P 9/00* | (2006.01) |

(52) U.S. Cl.
CPC .......... *A61K 31/726* (2013.01); *A61K 9/0019* (2013.01); *A61K 31/7008* (2013.01); *A61K 31/715* (2013.01); *A61K 45/06* (2013.01); *A61P 9/00* (2018.01)

(58) Field of Classification Search
CPC ............... A61K 31/722; A61K 31/726; A61K 31/7008; A61K 31/715; A61K 9/0019; A61K 45/06; A61P 9/00
See application file for complete search history.

(56) References Cited

U.S. PATENT DOCUMENTS

| | | |
|---|---|---|
| 5,624,679 A | 4/1997 | Vournakis et al. |
| 2005/0043272 A1 | 2/2005 | Platt et al. |
| 2010/0056474 A1* | 3/2010 | Baker ................... A61K 31/722 514/55 |
| 2014/0046052 A1 | 2/2014 | Daniels |
| 2014/0080785 A1* | 3/2014 | Baker ..................... A61P 31/00 514/54 |
| 2014/0154203 A1 | 6/2014 | Castillo et al. |

FOREIGN PATENT DOCUMENTS

EP 2759299 A1 7/2014

OTHER PUBLICATIONS

Angele et al., Critical Care, 2008, 12, article 218, 13 pages. (Year: 2008).*
Vogel et al., eds., Drug Discovery and Evaluation: Methods in Clinical Pharmacology, 2011, Springer-Verlag Berlin Heidelberg, pp. 173-180. (Year: 2011).*
Smucker P. et al., "Intravenous Polyethylene Glycol Successfully Treats Severe Acceleration-Induced Brain Injury In Rats As Assessed By Magnetic Resonance Imaging," Neurosurgery (2009), vol. 64, Issue 5, 984-990.
Supplementary EP Search Report for EP Application No. 16837600.2 dated Jul. 10, 2019 (15 pages).
International search report and written opinion of PCT/US2016/046829 dated Dec. 28, 2016 (10 pages).
Johansson et al., "A High Admission Syndecan-1 Level, A Marker of Endothelial Glycocalyx Degradation, Is Associated With Inflammation, Protein C Depletion, Fibrinolysis, and Increased Mortality in Trauma Patients", Annals of Surgery, vol. 254, No. 2, pp. 194-200, Aug. 2011.

* cited by examiner

*Primary Examiner* — Jonathan S Lau
(74) *Attorney, Agent, or Firm* — Goodwin Procter LLP

(57) ABSTRACT

Described herein are methods for treating inflammation, swelling and secondary damage of the vascular and lymphatic system in a subject, for example of the brain, spinal cord, and lungs; from organ reperfusion, e.g., resulting from endothelial leakage, glycocalyx dysfunction or loss of structural integrity of the glycocalyx.

16 Claims, 8 Drawing Sheets

DERIVATIZED CHITOSAN POLYMERS AND METHODS OF TREATING VASCULAR DISORDERS

RELATED APPLICATIONS

The present application is a Continuation of U.S. application Ser. No. 15/752,852, filed Feb. 14, 2018, which is a U.S. National Phase Application under 35 U.S.C. § 371 of International Application No. PCT/US2016/046829, filed Aug. 12, 2016, which claims the benefit of and priority to U.S. provisional application No. 62/205,408, filed Aug. 14, 2015, the contents of which are incorporated herein by reference in its-their entirety.

BACKGROUND OF INVENTION

Vascular disease includes any condition that affects the circulatory system, and ranges from diseases of the arteries, veins, and lymph vessels to blood disorders that affect circulation. The glycocalyx comprises a negatively charged network of proteoglycans, glycoproteins, and glycolipids with protective functions that are universal throughout the vascular system, with its relative importance varying depending on its exact location in the vasculature.

Polymers (e.g., cationic polymers) can provide stability and structure to the vasculature, e.g., via van der Waals interactions (e.g., hydrogen bonding) or charge-charge interactions (e.g., negative and positive charge interactions) with the polysaccharides in the glycocalyx. The polymers can provide stability and structure e.g., via positive charge interactions with the negatively charged glycocalyx. Development of polymers, e.g., that interact with the vasculature, e.g., the glycocalyx provide the basis for treatment of disorders of the vascular system, the brain, spinal cord, organs, lungs, and the lymphatic system that can result from dysfunction or loss of structural integrity of the glycocalyx.

SUMMARY OF INVENTION

Described herein are methods for treating disorders of the vascular system, the brain, spinal cord, organs, lungs, and the lymphatic system that can result from, e.g., dysfunction or loss of structural integrity of the glycocalyx (e.g., restores normal blood transport); by providing increased stability or structure, promoting endothelial integrity, restoring glycocalyx integrity, or reducing abnormal fluid transport across the glycocalyx.

In an aspect, described herein is a method of treating a disorder of the vascular system (e.g., the brain, spinal cord, organs, lungs, the lymphatic system), the method comprising intravenously administering a polymer (e.g., charged polysaccharide (e.g., polysaccharide conjugate)) to a subject, thereby treating the disorder. In some embodiments, the method restores normal blood transport or reduces abnormal fluid transport in the subject (e.g., relative to a subject without a disorder of the vascular system). In some embodiments, the method reduces the permeability of the blood brain barrier. In some embodiments, the method enhances the integrity of the blood brain barrier. In some embodiments, the method reduces VEGF-mediated deterioration.

In some embodiments, the disorder is inflammation, swelling and secondary damage of the vascular and lymphatic system. In some embodiments, the disorder is a result of dysfunction of the glycocalyx or loss of structural integrity of the glycocalyx, In some embodiments, the disorder is selected from brain injury (e.g., focal or diffuse brain injury), traumatic brain injury, concussion, stroke (e.g., hemorrhagic stroke, ischemic stroke), brain damage, ischemia, hemorrhagic shock, reperfusion injury, restenosis, acute respiratory distress syndrome, acute renal failure, sepsis, septic shock, lymphedema and spinal cord injury.

In some embodiments, the disorder is brain injury. In some embodiments, the brain injury is concussive brain injury. In some embodiments, the brain injury is moderate to severe brain injury. In some embodiments, the disorder is contrapoint injury. In some embodiments, the disorder is traumatic brain injury. In some embodiments, the disorder is suffering from hemorrhagic shock. In some embodiments, the disorder is suffering from ischemic and reperfusion injury. In some embodiments, the disorder is stroke. In some embodiments, the disorder is ischemic. In some embodiments, the disorder is hemorrhagic. In some embodiments, the disorder is acute macular degeneration of the eye. In some embodiments, the disorder is reperfusion injury in organ transplant. In some embodiments, the disorder is restenosis. In some embodiments, the disorder is an acute respiratory distress syndrome. In some embodiments, the disorder is an acute renal failure. In some embodiments, the disorder is septic shock. In some embodiments, the disorder is spinal cord injury. In some embodiments, the disorder is lymphedema.

In some embodiments, the polymer is soluble at physiologic pH (e.g., in blood (6-8)). In some embodiments, the polymer has a molecular weight (MW) between 30 and 300 kDa. In some embodiments, the polymer is 10-35% functionalized (e.g., with charged residue, e.g., arginine). In some embodiments, the polymer interacts with the glycocalyx surface (e.g., hydrogen bonding, electrostatic interactions, electrolytic interactions). In some embodiments, the polymer is a charged polymer. In some embodiments, the charged polymer is a polycationic polymer. In some embodiments, the polymer is a polysaccharide. In some embodiments, the polysaccharide is a polyglucosamine. In some embodiments, the polyglucosamine is a beta (1→4) polyglucosamine. In some embodiments, the polyglucosamine is a 1-6 or 1-3 polyglucosamine. In some embodiments, the polysaccharide is a polygalactosamine. In some embodiments, the polygalactosamine is a beta (1-3) or beta (1-4) galactosamine. In some embodiments, the polymer is a polypeptide. In some embodiments, the polymer is a synthetic, non-toxic polymer.

In some embodiments, the intravenous administration is by bolus administration. In some embodiments, the intravenous administration is by continuous infusion. In some embodiments, the administration is intraarterial.

In some embodiments, the method is administered less than 1, 2, 4, 6, 8, 12, 15, 18, 20, 24 hours, 1, 2, 3, 4, 5, 6, 7 days, 1, 2 weeks following injury.

In an aspect, described herein is a method of treating a disorder, wherein the disorder is dysfunction of the glycocalyx (e.g., reduces the protective barrier, causes internal fluid imbalance, edema, capillary leak, or adhesion) or loss of structural integrity of the glycocalyx, the method comprising intravenously administering a polymer (e.g., charged polysaccharide (e.g., polysaccharide conjugate)) to a subject, thereby treating the disorder.

In some embodiments, the method provides increased stability or structure, promotes endothelial integrity, restoring glycocalyx integrity, or reduces abnormal fluid transport across the glycocalyx (e.g., restores normal blood transport).

In some embodiments, the method reduces the permeability of the blood brain barrier. In some embodiments, the method enhances the integrity of the blood brain barrier.

In some embodiments, the method reduces VEGF-mediated deterioration.

DETAILED DESCRIPTION OF THE INVENTION

Figure 1:
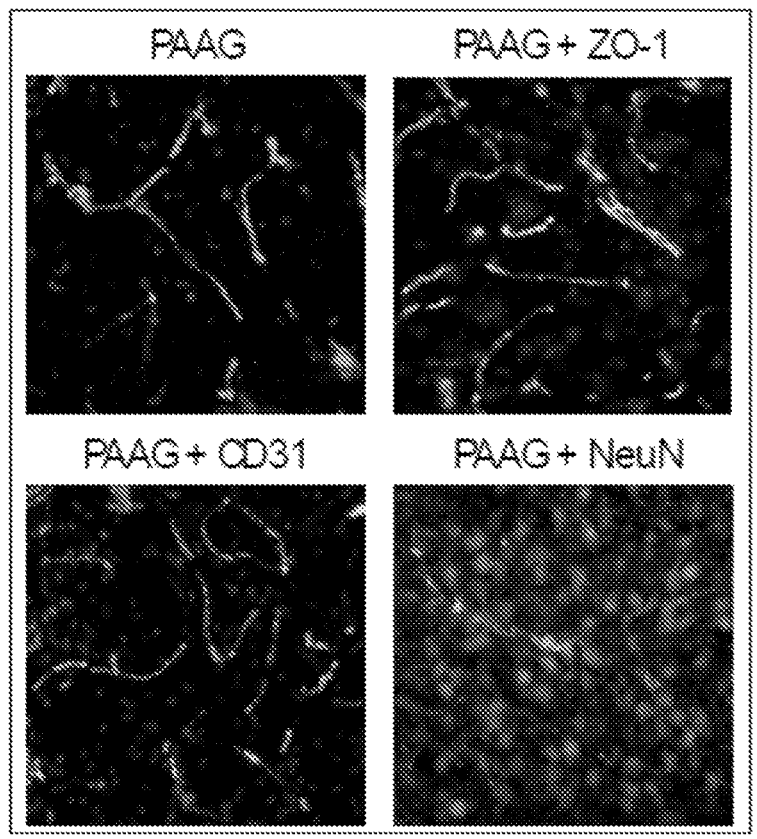
FIG. 1. Example images of the vascular networks 12 hours after staining with FITC-PAAG and antibodies for ZO-1, CD31 and NeuN.

Described herein are methods for treating inflammation, swelling and secondary damage of the vascular and lymphatic system, for example of the brain, spinal cord, and lungs; from organ reperfusion, resulting from endothelial leakage, glycocalyx dysfunction or loss of structural integrity of the glycocalyx in a subject. For example, methods described herein treat disorders that result from reduction of the protective barrier, internal fluid imbalance, edema, inflammation, capillary leak, or adhesion; or loss of structural integrity of the glycocalyx. The methods described herein treat disorders of the vascular system, the brain, spinal cord, organs, lungs, and the lymphatic system that can result from dysfunction or loss of structural integrity of the glycocalyx (e.g., restores normal blood transport) by providing increased stability or structure, promoting endothelial integrity, restoring glycocalyx integrity, or reducing abnormal fluid transport across the glycocalyx.

In some embodiments, the method reduces the permeability of the blood brain barrier. In some embodiments, the method enhances the integrity of the blood brain barrier.

Glycocalyx

The methods described herein treat disorders (e.g., of the vascular system, the brain, spinal cord, organs, lungs, and the lymphatic system) arising from or resulting in dysfunction of the glycocalyx or loss of structural integrity of the glycocalyx. The glycocalyx is located on the apical surface of vascular endothelial cells which line the lumen, and consists of a wide range of enzymes and proteins that regulate cellular and molecular adhesion and transport. A principal role of the glycocalyx in the vasculature is to maintain plasma and vessel wall homeostasis. Enzymes and proteins as well as other molecular entities serve to reinforce the glycocalyx barrier against vascular and other diseases. Another function of the glycocalyx within the vascular endothelium is to shield the vascular walls from direct exposure to blood flow, while serving as a vascular permeability barrier. Its protective functions are universal throughout the vascular system, with its relative importance varying depending on its exact location in the vasculature. The glycocalyx comprises a negatively charged network of proteoglycans, glycoproteins, and glycolipids. The glycocalyx is involved in the filtration of fluid from the plasma to the interstitial space, protection of the endothelium from blood cell adhesion, mediation of the signal for nitric oxide (NO) production by endothelial cells. As a result, the glycocalyx serves as a protective barrier for the important vascular systems such as the brain, spinal cord, organs, lungs and lymphatic system that are susceptible to injury from damage to the glycocalyx or disruption of glycocalyx function.

Alteration of the glycocalyx is involved in endothelial damage, e.g., caused by sepsis, localized or systemic inflammation; compromising endothelial permeability that is associated with interstitial fluid shift and generalized edema. Such changes in the endothelial glycocalyx are linked to loss of vascular tone, hypovolemia, edema formation, and organ dysfunction. Subjects with perturbed glycocalyx may have impaired protective function and increased vascular vulnerability, e.g., accelerating atherosclerosis. Impaired glycocalyx structure or function can also be associated with renal failure (e.g., acute, chronic), chronic kidney disease.

Disorders

The methods described herein treat a variety of disorders (e.g., of the vascular system, the brain, spinal cord, organs, lungs, and the lymphatic system) that can arise from the dysfunction or loss of structural integrity of the endothelial glycocalyx. The disorders can result from injuries resulting in a proinflammatory environment in the vasculature or an inflammatory (or immune) attack on the vasculature. Exemplary disorders treated by the methods described herein include brain injury (e.g., focal or diffuse brain injury), traumatic brain injury, concussion, stroke (e.g., hemorrhagic stroke, ischemic stroke), brain damage, ischemia, hemorrhagic shock, reperfusion injury, restenosis, acute respiratory distress syndrome, acute renal failure, sepsis, septic shock, lymphedema and spinal cord injury.

In some embodiments, the disorder treated by the methods described herein is contrapoint injury. In some embodiments, the disorder is hemorrhagic shock. In some embodiments, the disorder is ischemic and reperfusion injury. In some embodiments, the disorder is acute macular degeneration of the eye. In some embodiments, the disorder is reperfusion injury in organ transplant. In some embodiments, the disorder is restenosis. In some embodiments, the disorder is an acute respiratory distress syndrome. In some embodiments, the disorder is an acute renal failure. In some embodiments, the disorder is septic shock. In some embodiments, the disorder is spinal cord injury. In some embodiments, the disorder is lymphedema.

The following exemplary disorders treated by the methods described herein are injuries that result in a breakdown of the integrity of the vascular endothelia, e.g., leading to translocation of proteins, ions and molecules across the vascular endothelia, leading to edema, inflammation, swelling and secondary damage.

Brain injury refers to any injury to the brain of a living organism, for example injury caused by a violent blow to the head. Focal brain injury refers to injury to a specific location, while diffuse brain injury refers to injury over a more widespread area. Focal and diffuse brain injury can occur as a result of the same event, e.g., physical trauma or other types of brain injury (such as stroke). Brain injury can be characterized as moderate to severe. Specific forms of brain injury include brain damage, traumatic brain injury, and stroke.

Brain damage is the destruction or deterioration of brain cells. Generally, brain damage refers to significant, undiscriminating trauma-induced damage.

Traumatic brain injury (TBI) occurs when an external force injures the brain. Brain trauma can occur as a consequence of a focal impact upon the head, by a sudden acceleration/deceleration within the cranium or by a combination of both movement and sudden impact. TBI often causes secondary injury from a cascade of events that occur in the days following the injury. The events include alterations in cerebral blood flow and pressure within the skull, which contribute substantially to the damage from the initial injury. Concussion or concussive brain injury refers to a traumatic brain injury that alters the way that the brain functions. Concussions can be caused by a blow to the head or body, or a fall or other injury that shakes the brain inside the skull. Symptoms of concussion include passing out, loss of memory, seizures, trouble walking or sleeping, weakness, numbness, decreased coordination, repeated vomiting or nausea, confusion, or slurred speech; and can range from mild to severe. Symptoms of concussion can last for hours, days, weeks, or months.

Stroke is a vascular event causing brain damage. A hemorrhagic stroke results from a weakened vessel that ruptures and bleeds into the surrounding brain. Aneurysms and arteriovenous malformations are two types of weakened blood vessels that can cause hemorrhagic stroke. Hemorrhagic stroke can be intracerebral (within the brain) hemorrhage or subarachnoid hemorrhage. Symptoms of intracerebral hemorrhage include sudden weakness, paralysis or numbness in any part of the body, inability to speak, inability to control eye movements correctly, vomiting, irregular breathing, stupor, and coma. Symptoms of subarachnoid hemorrhage include a very severe headache that starts suddenly, loss of consciousness, nausea and vomiting, inability to look at bright light, stiff neck, dizziness, confusion, seizure, and loss of consciousness. An ischemic stroke is characterized by the sudden loss of blood circulation to an area of the brain that results in a loss of neurologic function. For example, acute ischemic stroke is caused by thrombotic or embolic occlusion of a cerebral artery and is more common than hemorrhagic stroke. Symptoms of an ischemic stroke include trouble with speaking and understanding, paralysis or numbness of the face, arm or leg, trouble with seeing in one or both eyes, headache, and trouble with walking.

Ischemia or an "ischemic event" is a vascular disease generally involving vascular occlusion or a restriction in blood supply to tissues. Ischemia can cause a shortage of oxygen and glucose needed for cellular metabolism. Ischemia is generally caused by problematic blood vessels that result in damage or dysfunction of tissue. Ischemia can also refer to a local loss in blood or oxygen in a given part of the body resulting from congestion (e.g., vasoconstriction, thrombosis, or embolism). Causes include embolism, thrombosis of an atherosclerosis artery, trauma, venous problems, aneurysm, heart conditions (e.g., myocardial infarction, mitral valve disease, chronic arterial fibrillation, cardiomyopathies, and prosthesis), trauma or traumatic injury (e.g., to an extremity producing partial or total vessel occlusion), thoracic outlet syndrome, atherosclerosis, hypoglycemia, tachycardia, hypotension, outside compression of a blood vessel (e.g., by a tumor), sickle cell disease, localized extreme cold (e.g., by frostbite), tourniquet application, glutamate receptor stimulation, arteriovenous malformations, rupture of significant blood vessels supplying a tissue or organ, and anemia.

A transient ischemic event generally refers to a transient (e.g., short-lived) episode of neurologic dysfunction caused by loss of blood flow (e.g., in the focal brain, spinal cord, or retinal) without acute infarction (e.g., tissue death). In some embodiments, the transient ischemic event lasts for less than 72 hours, 48 hours, 24 hours, 12 hours, 10 hours, 8 hours, 4 hours, 2 hours, 1 hour, 45 minutes, 30 minutes, 20 minutes, 15 minutes, 10 minutes, 5 minutes, 4 minutes, 3 minutes, 2 minutes, or 1 minute.

Hemorrhagic shock occurs when there is heavy bleeding such that not enough blood flows to the bodily organs. Because blood carries oxygen and other essential substances to the organs and tissues, heavy bleeding can cause the organs of the body to begin to shut down. Common causes of hemorrhagic shock include severe burns, deep cuts, gunshot wounds, trauma, and amputations. Symptoms of hemorrhagic shock include anxiety, blue lips and fingernails, low or no urine output, profuse sweating, shallow breathing, dizziness, confusion, chest pain, loss of consciousness, low blood pressure, rapid heart rate, and weak pulse.

Reperfusion injury refers to the tissue damage caused when blood supply returns to the tissue after a period of ischemia or lack of oxygen. Restoration of circulation may result in inflammation and oxidative damage through the induction of oxidative stress. In some embodiments, reperfusion injury follows organ transplant.

Restenosis refers to the narrowing of a blood vessel (e.g., an artery, a vessel within an organ) that leads to restricted blood flow.

Acute respiratory distress syndrome (ARDS) is a life-threatening lung condition that prevents sufficient oxygen from getting to the lungs and into the blood. ARDS usually develops in people who are already very ill. A person with ARDS has rapid breathing, difficulty getting enough air into the lungs, and low blood oxygen levels.

Acute renal failure refers to the sudden inability of the kidneys to filter waste products from the blood. Acute renal failure is also referred to as acute kidney injury, and can develop rapidly (e.g., over a few hours, over a few days).

Sepsis is a potentially life-threatening complication of an infection that can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). Sepsis can occur when chemicals released into the bloodstream to fight infection trigger inflammatory responses throughout the body. The inflammation can trigger a cascade of changes that can damage multiple organ systems, causing them to fail. Sepsis can progress to septic shock, where blood pressure drops dramatically and can lead to death. Septic shock occurs as a complication of an infection, where toxins can initiate a full-body inflammatory response. Septic shock can occur when the blood pressure drops to a dangerously low level after an infection.

Spinal cord injury refers to an injury to the spinal cord that results in a temporary or permanent change in the cord's normal motor, sensory, or autonomic function. Spinal cord injury typically results from a sudden, traumatic blow to the spine that fractures or dislocates the vertebrae.

Compounds

The polymers described herein are administered parenterally (e.g., intravenous injection) and are active on the endothelial surface, i.e. at the glycocalyx layer. The polymer protects endothelial vascular tissue from fluid leakage (e.g., by interacting with the glycocalyx). By interacting with the glycocalyx, the compounds may provide stability and structure, e.g., to promote endothelial intra adhesion and reduce abnormal fluid transport across the glycocalyx, thereby treating a disorder described herein.

In some embodiments, the compounds provide stability and structure via van der Waals interactions (i.e., hydrogen bonding) with the polysaccharides in the glycocalyx. In some embodiments, the compounds provide stability and structure via positive charge interactions with the negative glycocalyx. In some embodiments, the compounds provide stability and structure via partitioning from the blood volume to the surface and intercolation into the glycocalyx. In some embodiments, the compounds provide stability and structure via partitioning from the blood volume to the surface of the endothelial cells.

The polymer useful for this application is soluble at physiologic pH (e.g., in blood (6-8)). In some embodiments, the polymer has a molecular weight (MW) between 30 and 300 kDa. In some embodiments, the polymer is a polysaccharide. In some embodiments, the polysaccharide is a polyglucosamine. In some embodiments, the polysaccharide is a polygalactosamine. In some embodiments, the polymer is a polypeptide. In some embodiments, the polymer is a synthetic, non-toxic polymer.

In some embodiments, the polymer interacts (e.g., via van der Waals interactions, electrostatic interactions, charge-charge interactions, hydrogen bonding interactions, cation-anion interactions) on the surface of the glycocalyx at physiological pH.

In some embodiments, the method provides increased stability or structure, promotes endothelial intra adhesions, restoring glycocalyx integrity, or reduces abnormal fluid transport across the glycocalyx.

In some embodiments, the polymer described herein comprises a "cationic moiety" or "cationic moieties." The term "cationic moiety" or "cationic moieties" refers to a moiety or moieties that have a pKa 5 or greater (e.g., a Lewis base having a pKa of 5 or greater) and or a positive charge in at least one of the following conditions: during the production of a polymer as described herein, or subsequent to administration of a polymer as described herein to a subject. Exemplary cationic moieties include amine groups (e.g., charged amine groups such as a primary, secondary, tertiary or quaternary amine, guanidine-containing moieties (e.g., a charged guanidine such as a guanidium moiety), and heterocyclic and or heteroaromatic moieties (e.g., charged moieties such as a pyridinium or a histidine moiety). A "cationic polymer" refers to a polymer that has a plurality of positive charges (i.e., at least 2) when synthesized or formulated. In some embodiments, the cationic polymer, for example, a polyamine, has at least 3, 4, 5, 10, 15, or 20 positive charges. In some embodiments, the polymer (e.g., polysaccharide, polypeptide or synthetic polymer) is positively charged, e.g., by modification by or inclusion of charged amino acids. In some embodiments, the polymer comprises between 10-50% arginine. In some embodiments, the polymer comprises between 10-50% lysine. In some embodiments, the polymer comprises between 10-50% natural or unnatural cationic amino acids.

Exemplary cationic moieties include amines, for example, primary, secondary, tertiary, and quaternary amines, and polyamines (e.g., branched and linear polyethylene imine (PEI) or derivatives thereof such as polyethyleneimine-PLGA, polyethylene imine-polyethylene glycol-N-acetylgalactosamine (PEI-PEG-GAL) or polyethylene imine-polyethylene glycol-tri-N-acetylgalactosamine (PEI-PEG-triGAL) derivatives). In some embodiments, the cationic moiety comprises a cationic lipid (e.g., 1-[2-(oleoyloxy)ethyl]-2-oleyl-3-(2-hydroxyethyl)imidazolinium chloride (DOTIM), dimethyldioctadecyl ammonium bromide, 1,2 dioleyloxypropyl-3-trimethyl ammonium bromide, DOTAP, 1,2-dimyristyloxypropyl-3-dimethyl-hydroxyethyl ammonium bromide, 1,2-dimyristoyl-sn-glycero-3-ethylphosphocholine (EDMPC), ethyl-PC, 1,2-dioleoyl-3-dimethylammonium-propane (DODAP), DC-cholesterol, and MBOP, CLinDMA, 1,2-dilinoleyloxy-3-dimethylaminopropane (DLinDMA), pCLinDMA, eCLinDMA, DMOBA, and DMLBA). In some embodiments, for example, where the cationic moiety is a polyamine, the polyamine comprises, polyamino acids (e.g., poly(lysine), poly(histidine), and poly(arginine)) and derivatives (e.g. poly(lysine)-PLGA, imidazole modified poly(lysine)) or polyvinyl pyrrolidone (PVP). In some embodiments, for example, where the cationic moiety is a cationic polymer comprising a plurality of amines, the amines can be positioned along the polymer such that the amines are from about 4 to about 10 angstroms apart (e.g., from about 5 to about 8 or from about 6 to about 7). In some embodiments, the amines can be positioned along the polymer so as to be in register with phosphates on a nucleic acid agent. The cationic moiety can have a pKa of 5 or greater and/or be positively charged at physiological pH.

In some embodiments, the cationic moiety includes at least one amine (e.g., a primary, secondary, tertiary or quaternary amine), or a plurality of amines, each independently a primary, secondary, tertiary or quaternary amine). In some embodiments the cationic moiety is a polymer, for example, having one or more secondary or tertiary amines, for example cationic polyvinyl alcohol, polyamine-branched and star PEG and polyethylene imine.

In some embodiments, the cationic moiety includes a nitrogen containing heterocyclic or heteroaromatic moiety (e.g, pyridinium, immidazolium, morpholinium, piperizinium, etc.). In some embodiments, the cationic polymer comprises a nitrogen containing heterocyclic or heteroaromatic moiety such as polyvinyl pyrolidine or polyvinylpyrolidinone.

In some embodiments, the cationic moiety includes a guanidinium moiety (e.g., an arginine moiety). In some embodiments, the polymer (e.g., polysaccharide, polypeptide or synthetic polymer) is positively charged by modification with acid amines or acid guanidines.

Additional exemplary cationic moieties include agamatine, protamine sulfate, hexademethrine bromide, cetyl trimethylammonium bromide, 1-hexyltriethyl-ammonium phosphate, 1-dodecyltriethyl-ammonium phosphate, spermine (e.g., spermine tetrahydrochloride), spermidine, and derivatives thereof (e.g. N1-PLGA-spermine, N1-PLGAN5, N10, N14-trimethylated-spermine, (N1-PLGA-N5,N10,N14, N14-tetramethylated-spermine), PLGA-glu-di-triCbz-spermine, triCbz-spermine, amiphipole, PMAL-C8, and acetyl-PLGA5050-glu-di(N1-amino-N5,N10,N14-spermine), poly (2-dimethylamino)ethyl methacrylate), hexyldecyltrimethylammonium chloride, hexadimethrine bromide, and atelocollagen.

The term "polymer" as used herein is given its ordinary meaning as used in the art, i.e., a molecular structure featuring one or more repeat units (monomers), connected by covalent bonds. The repeat units may be all identical, or in some cases, there may be more than one type of repeat unit present within the polymer. Polymers may be natural or unnatural (i.e., synthetic) polymers. Polymers may be homopolymers or copolymers containing two or more monomers. Polymers may be linear or branched.

In some embodiments, the polymer is a soluble polygalactosamine or polygalactosamine derivative. In some embodiments, the soluble polygalactosamines or derivatized polygalactosamine is connected by a beta (1→3) linkage or beta (1→4) linkage. In some embodiments, the polymer is a soluble polyglucosamine or polyglucosamine derivative. In some embodiments, the soluble polyglucosamine or derivatized polyglucosamine is connected by a β(1→4), (1→6) linkage or (1→3) linkage.

In some embodiments, the polysaccharide, polypeptide or synthetic polymer is not modified (e.g., does not have a net positive charge) but remains soluble.

If more than one type of repeat unit is present within the polymer, then the polymer is a "copolymer." It is to be understood that in any embodiment employing a polymer, the polymer being employed may be a copolymer. The repeat units forming the copolymer may be arranged in any fashion, e.g., the repeat units may be arranged in random order, in an alternating order, or as a "block" copolymer, i.e., containing one or more regions each containing a first repeat unit (e.g., a first block), and one or more regions each containing a second repeat unit (e.g., a second block), etc. Block copolymers may have two (a diblock copolymer), three (a triblock copolymer), or more numbers of distinct blocks. In terms of sequence, copolymers may be random, block, or contain a combination of random and block sequences.

In some embodiments, the polymer is biologically derived, i.e., a biopolymer. Non-limiting examples of biopolymers include peptides or proteins (i.e., polymers of various amino acids), or nucleic acids such as DNA or RNA. In some embodiments, the polymer is a polypeptide. In some embodiments, the polymer is a polysaccharide.

As used herein, "polymer polydispersity index (PDI)" or "polymer polydispersity" refers to the distribution of molecular mass in a given polymer sample. The polymer PDI calculated is the weight average molecular weight divided by the number average molecular weight. The PDI indicates the distribution of individual molecular masses in a batch of polymers. The polymer PDI has a value typically greater than 1, but as the polymer chains approach uniform chain length, the PDI approaches unity (1).

Soluble Polyglucosamines and Polyglucosamines Derivatives

Compounds and compositions containing a soluble polyglucosamine or a derivatized polyglucosamine for treating or preventing a disease or symptom of a disease described herein, e.g., brain injury.

Polyglucosamines can be derived from chitin or chitosan. Chitosan is an insoluble polymer derived from the deacetylation of chitin, which is a polymer of N-acetylglucosamine, that is the main component of the exoskeletons of crustaceans (e.g., shrimp, crab, lobster). Chitosan is generally a β(1→4) polyglucosamine that is less than 50% acetylated while chitin is generally considered to be more than 50% acetylated. Polyglucosamines are also found in various fungi and arthropods. Synthetic sources and alternate sources of β(1→4) polyglucosamines may serve as the starting material for polyglucosamine derivatives. Polyglucosamines may also be connected by a 1→6 linkage or 1→3 linkage or contain glucan sidechains (i.e. f-glucans). Polyglucosamines, as opposed to polyacetylglucosamines, are defined herein to be less than 50% acetylated. If greater than 50% of the amino groups are acetylated, the polymer is considered a polyacetylglucosamine.

A soluble polyglucosamine described herein refers to a neutral pH, water soluble polyglucosamine or polyglucosamine that is not derivatized on the hydroxyl or amine moieties other than with acetyl groups. A soluble polyglucosamine comprises glucosamine and acetylglucosamine monomers. Generally, a water soluble polyglucosamine (at neutral pH) has a molecular weight of less than or equal to about 5,000 kDa and a degree of deacetylation equal to or greater than 80%.

A polyglucosamine derivative described herein is generated by functionalizing the free hydroxyl or amine groups with positively charged or neutral moieties. The percent of functionalization is defined as the total percent of monomers on the polyglucosamine backbone that have been functionalized with a positively charged or neutral moiety. The degrees of deacetylation and functionalization impart a specific charge density to the functionalized polyglucosamine derivative. The resulting charge density affects solubility and effectiveness of treatment. Thus, in accordance with the present invention, the degree of deacetylation, the functionalization and the molecular weight must be optimized for optimal efficacy. The polyglucosamine derivatives described herein have a number of properties which are advantageous, including solubility at physiologic (neutral) pH. In some embodiments, the polyglucosamine derivative is soluble up to a pH of 10. The polyglucosamine derivative described herein is soluble at pH 2 to pH 10. The polyglucosamine derivative described herein is soluble at pH 5 to pH 9. The polyglucosamine derivative described herein is soluble at pH 6 to pH 8. The polyglucosamine derivative described herein is soluble at pH 6.5 to pH 8. The polyglucosamine derivative described herein is soluble at pH 7 to pH 8. In some embodiments, the molecular weight of the polyglucosamine derivative is between 15 and 350 kDa. In some embodiments, the molecular weight of the polyglucosamine derivative is between 25 and 250 kDa. In some embodiments, the molecular weight of the polyglucosamine derivative is between 30 and 150 kDa.

Polyglucosamines with any degree of deacetylation (DDA) greater than 50% are used in the present invention, with functionalization between 2% and 50% of the total monomers on the polyglucosamine backbone. The degree of deacetylation determines the relative content of free amino groups to total monomers in the polyglucosamine polymer. Methods that can be used for determination of the degree of deacetylation of polyglucosamine include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble polyglucosamine or a derivatized polyglucosamine described herein is determined by quantitative infrared spectroscopy.

Percent functionalization by active derivitization of the amines is determined relative to the total number of monomers on the polyglucosamine polymer. Preferably, the percent functionalization of a derivatized polyglucosamine described herein is determined by H-NMR or quantitative elemental analysis. The degrees of deacetylation and functionalization impart a specific charge density to the functionalized polyglucosamine derivative. The resulting charge density affects solubility, and strength of interaction with tissue, biofilm components and bacterial membranes. The molecular weight is also an important factor in a derivatized polyglucosamine's mucoadhesivity and biofilm disrupting capability. Thus, in accordance with the present invention, these properties must be optimized for optimal efficacy. Exemplary polyglucosamine derivatives are described in U.S.P.N. 8,119,780, which is incorporated herein by reference in its entirety.

The polyglucosamine derivatives described herein have a range of polydispersity index (PDT) between about LG to about 3.0. The polyglucosamine derivatives described herein have a range of polydispersity index (PDI) between about 1.2 to about 2.8. The polyglucosamine derivatives described herein have a range of polydispersity index (PDI) between about L 0.0 to about 2.5. The polyglucosamine derivatives described herein have a range of polydispersity index (PDI) between about 1.5 to about 2.0. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g., chitin or chitosan from crab vs. shrimp vs. fungi) and is modified or controlled by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble polyglucosamine or a derivatized polyglucosamine described herein is determined by HPLC and multi angle light scattering methods.

The polyglucosamine derivatives (i.e., derivatized polyglucosamines) described herein have a variety of selected molecular weights that are soluble at neutral and physiological pH, and include for the purposes of this invention molecular weights ranging from 5-1,000 kDa. Derivatized polyglucosamines are soluble at pH up to about 10. Embodiments described herein are medium range molecular weight derivatized polyglucosamines (30-150 kDa, e.g., from about 30 to about 150 kDa). In some embodiments, the molecular weight of the derivatized polyglucosamine is between 10 and 1,000 kDa. In some embodiments, the molecular weight of the derivatized polyglucosamine is between 15 and 350 kDa.

In some embodiments, the molecular weight of the derivatized polyglucosamine is between 20 and 200 kDa. In some embodiments, the molecular weight of the functionalized polyglucosamine is between 30 and 150 kDa.

The functionalized polyglucosamine derivatives described herein include the following:

(A) Polyglucosamine-arginine compounds;
(B) Polyglucosamine-natural amino acid derivative compounds;
(C) Polyglucosamine-unnatural amino acid compounds;
(D) Polyglucosamine-acid amine compounds;
(E) Polyglucosamine-guanidine compounds; and
(F) Neutral polyglucosamine derivative compounds.

(A) Polyglucosamine-Arginine Compounds

In some embodiments, the polymers described herein are polyglucosamine-arginine compounds, where the arginine is bound through a peptide (amide) bond via its carbonyl to the primary amine on the glucosamines of polyglucosamine:

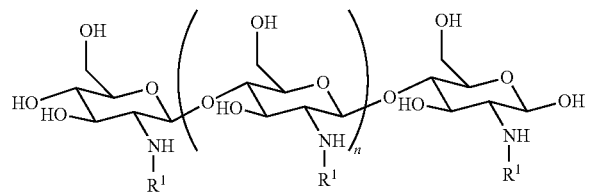

wherein each $R^1$ is independently selected from hydrogen, acetyl, and a group of the following formula:

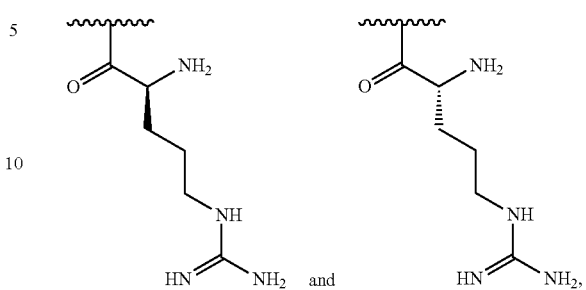

or a racemic mixture thereof, wherein at least 25% of $R^1$ substituents are H, at least 1% are acetyl, and at least 2% are a group of the formula shown above.

In some embodiments, a polyglucosamine-arginine compound is of the following formula

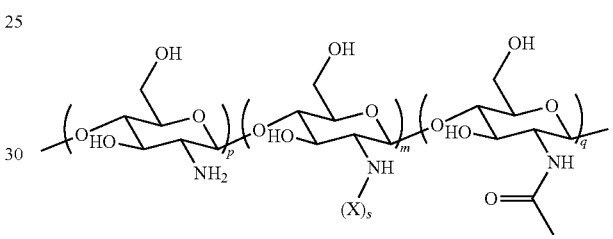

where m is 0.02-0.50; q is 0.50-0.01; s is 1; p+q+m=1; the percent degree of functionalization is m·100%; and X is selected from the group consisting of:

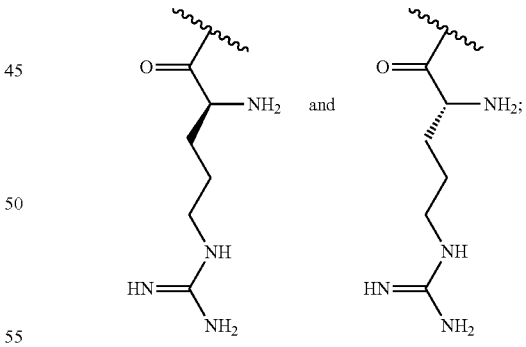

wherein the preparation is substantially free of compounds having a molecular weight of less than 5 kDa.

(B) Polyglucosamine-Natural Amino Acid Derivative Compounds

In some embodiments, the polymers described herein are polyglucosamine-natural amino acid derivative compounds, wherein the natural amino acid may be histidine or lysine. The amino is bound through a peptide (amide) bond via its carbonyl to the primary amine on the glucosamines of polyglucosamine:

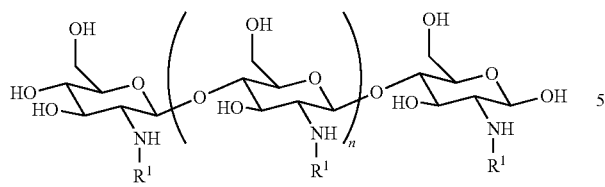

wherein each $R^1$ is independently selected from hydrogen, acetyl, and a group of the following formula:

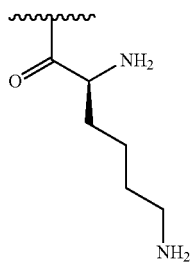

or a racemic mixture thereof, wherein at least 25% of $R^1$ substituents are H, at least 1% are acetyl, and at least 2% are a group of the formula shown above; or a group of the following formula:

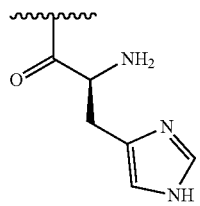

or a racemic mixture thereof, wherein at least 25% of $R^1$ substituents are H, at least 1% are acetyl, and at least 2% are a group of the formula shown above.

(C) Polyglucosamine-Unnatural Amino Acid Compounds

In some embodiments, the polymers described herein are polyglucosamine-unnatural amino acid compounds, where the unnatural amino acid is bound through a peptide (amide) bond via its carbonyl to the primary amine on the glucosamines of polyglucosamine:

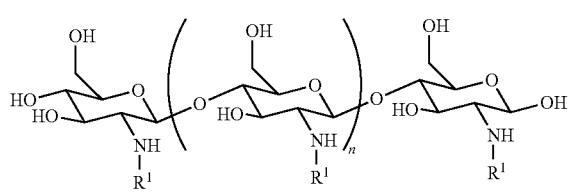

wherein each R is independently selected from hydrogen acetyl, and a group of the following formula:

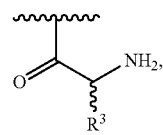

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to polyglucosamine have the following formulae:

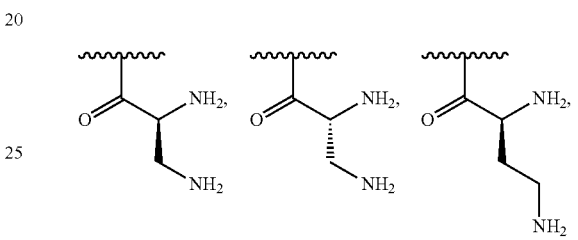

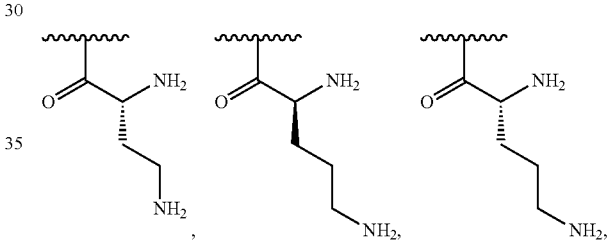

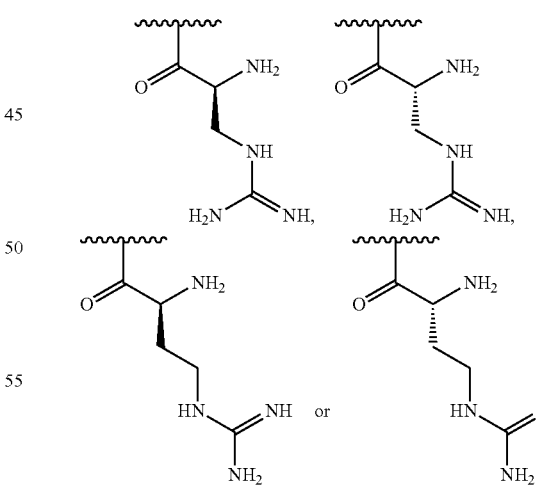

(D) Polyglucosamine-Acid Amine Compounds

In some embodiments, the polymers described herein are polyglucosamine-acid amine compounds, or their guanidylated counterparts. The acid amine is bound through a peptide (amide) bond via its carbonyl to the primary amine on the glucosamines of polyglucosamine:

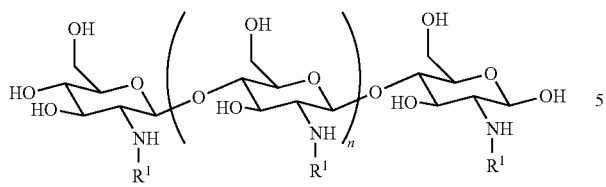

wherein each R is independently selected from hydrogen acetyl, and a group of the following formula:

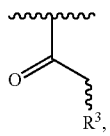

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

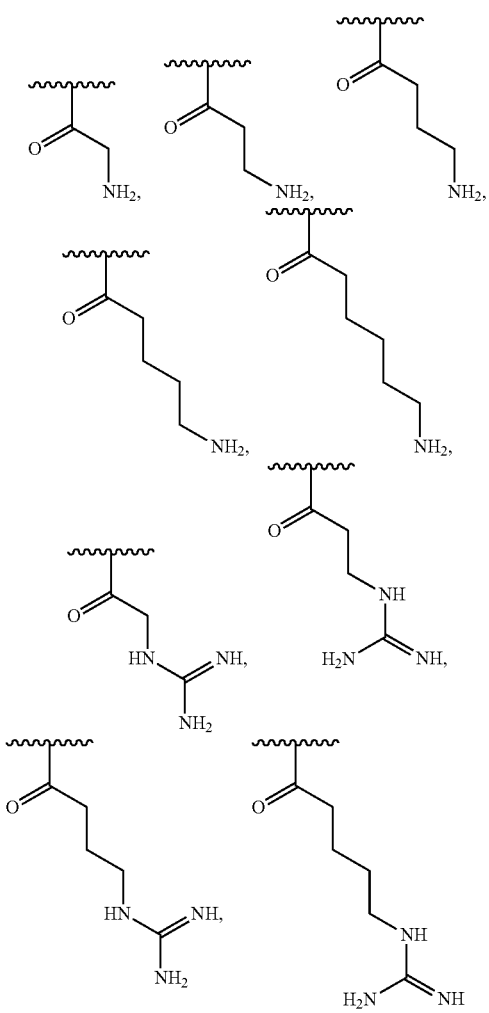

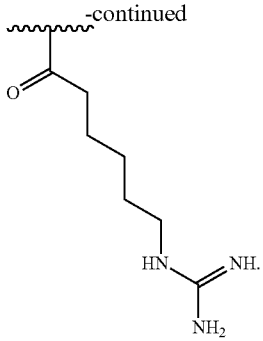

(E) Polyglucosamine-Guanidine Compounds

In some embodiments, the polymers described herein are polyglucosamine-guanidine compounds.

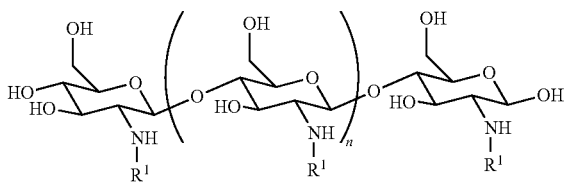

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Polyglucosamine Derivative Compounds

In some embodiments, the polymers described herein are neutral polyglucosamine derivative compounds. Exemplary neutral polyglucosamine derivative compounds include those where one or more amine nitrogens of the polyglucosamine have been covalently attached to a neutral moiety such as a sugar:

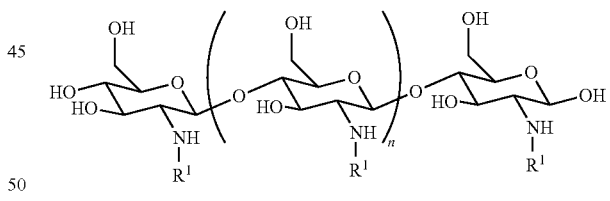

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some preferred embodiments, the neutral polyglucosamine derivative is polyglucosamine-lactobionic acid compound or polyglucosamine-glycolic acid compound. Exemplary salts and coderivatives include those known in the art, for example, those described in U.S. Pat. No. 8,119,780, the contents of which is incorporated by reference in its entirety, Routes of Administration The methods described herein may be administered parenterally (e.g., by intravenous infusion, e.g., intravenous bolus injection, intravenous continuous infusion). The methods described may be used to deliver the polymers described herein in any conventional non-toxic pharmaceutically-acceptable carriers, adjuvants or vehicles. In some embodiments, the pH of the composition (e.g., composition comprising a polymer as described herein) may be adjusted with pharmaceutically acceptable acids, bases or buffers to enhance the stability of the polymer.

The composition described herein may be in the form of a sterile injectable preparation, for example, as a sterile injectable aqueous solution or suspension. The sterile injectable preparation may be a sterile injectable solution or suspension in a non-toxic parenterally acceptable diluent or solvent. Sterile, fixed oils may be employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. Surfactants such as Tweens or Spans or other emulsifying agents or bioavailability enhancers may also be used. Some examples of solvents or suspending medium suitable for preparation of sterile injectables include a preparation comprising 1,3-butanediol, mannitol, water, Ringer's solution, isotonic sodium chloride solution, ethanol, glycerol, propylene glycol, liquid polyethylene glycol, cyclodextrin derivatives, or vegetable oils.

The polymers described herein can, for example, be administered by injection, intravenously (e.g., intravenous infusion, intravenous bolus injection), with a dosage ranging from about 0.5 to about 100 mg/kg of body weight, alternatively dosages between 1 mg and 1000 mg/dose, e.g., every 4 to 120 hours. In some embodiments, the polymers described herein are administered intraarterially. The methods herein contemplate administration of an effective amount of polymer or polymer composition to achieve the desired or stated effect. Typically, the polymers provided herewith will be administered from about 1 to about 3 times per day, 2 days, 3 days, 4 days, 5 days, 6 days, or 7 days, 1 week, 2 weeks, or 3 weeks (e.g., by intravenous bolus injection) or alternatively, as a continuous infusion. The amount of active ingredient that may be combined with the carrier materials to produce a single dosage form will vary depending upon the host treated and the particular mode of administration. A typical preparation will contain from about 5% to about 95% (e.g., about 20% to about 80%) polymer (w/w).

Kits

Also described herein are kits comprising a polymer as described herein. In some embodiments, the polymer described herein is provided in a composition (e.g., an aqueous composition, an aqueous solution). In some embodiments, the composition comprising the polymer described herein is provided in a container. For example, the composition comprising the polymer described herein can be provided in a bag (e.g., plastic or polymer bag), vial, bottle, or syringe. In addition, the kit comprising a polymer described herein (e.g, a composition comprising a polymer as described herein), may be accompanied by instructions for administration. The kit may be accompanied by a notice in a form prescribed by a governmental agency regulating the manufacture, use, or sale of pharmaceuticals, which notice is reflective of approval by the agency of the form of the compositions for human administration. For example, such notice may be of labeling approved by the U.S. Food and Drug Administration for prescription drugs or of approved product insert.

EXAMPLES

Example 1. Distribution of Intravenous Injection of PAAG in the Brain after Injury Nine mice received TBI's inflicted with a controlled cortical impactor (injury depth 1.15 mm at 4.0 m/sec). All mice received an IV injection of PAAG via tail vein at one of three concentrations (8 mg/kg, 40 mg/kg, 80 mg/kg PAAG in saline). The brains were then harvested one hour, four hours, 12 hours after PAAG injection so that one brain was harvested for each time point/dose combination. The brains were then sectioned and imaged on DM6000 microscope (Leica) at 50, 100, and 200 magnification.

PAAG intensity increased over time in the vasculature and also in the penumbra of the injury on the ipsilateral side. FITC PAAG accumulated along the vessel walls, revealing the vascular network in the brain in sections taken from brains harvested 4 and 12 hours after being treated with the highest dose of PAAG and 12 hours after being treated with medium dose. Presence of PAAG was visible however at 1 hour post delivery in the 80 mg/kg dose on the ipsilateral side. To confirm that the FITC-PAAG was attached/proximal to the brain's endothelium we performed immunohistochemistry for endothelial markers ZO-1 and CD31. ZO-1 is a component of the endothelial tight junctions and CD31 is the platelet endothelial cell adhesion molecule (PECAM-1) which is present predominantly on endothelial cells. Both antibodies co-localize with PAAG in the vessel. Also demonstrated was that PAAG was present close to the neurovascular units, depicted by proximity of NeuN and PAAG staining. FIG. 1 provides example images of the vascular networks revealed by 80 mg/kg FITC-PAAG (green) and co-stained with antibodies for ZO-1, CD31 and NeuN (red). Yellow indicates costaining. Images taken 12 hours after treatment. PAAG was present in the brain after IV delivery and localized to the vasculature and in the injured hippocampus.

Example 2. Effects of PAAG on Blood Brain Barrier Permeability Induced by TBI

Injury Depth 1.3 mm at 4.0 m/Sec

Figure 2:
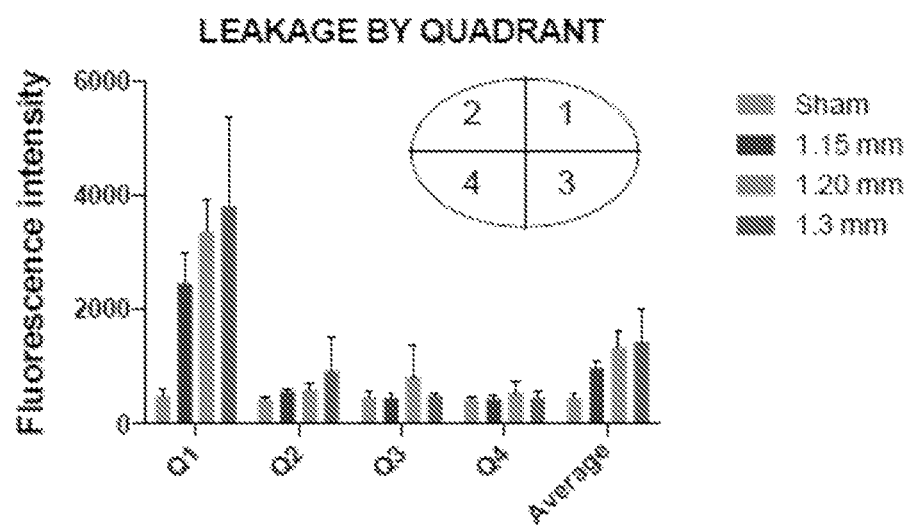
FIG. 2. Quantitation of vascular leak 3 days after TBI for animals treated with PAAG or control (n=5/arm), examining different penetration depths of the dye.

Mice received 8 mg/kg PAAG or saline via tail vein (5 animals/group) four hours before sacrifice three days after TBI. One hour before sacrifice, the mice received 200 ul of 1 mg/mL 10 kDa dextran conjugated with 680 Alexa Fluor-infrared dye. Mice were perfused with 60 mL ice cold PBS at a rate of 4 mL/min via the left cardiac ventricle. The brain was then sectioned into 2 mm wide sections and scanned on a Li-Cor odyssey scanner (Li-Cor Bioscience, Inc.). Each section was divided into quadrants and the average fluorescence intensity was calculated for each quadrant using Image Studio (Li-Cor Bioscience, Inc.). To quantitate the quadrant intensity for each brain, the average fluorescence intensity from three serial sections with the middle section containing the center of the injury site were averaged and normalized to Q1 of the control. This injury level was chosen based on a preliminary experiment that determined the vascular leakage with injury depths of 1.3 mm, 1.2 mm, and 1.15 mm as shown in FIG. 2. Trends to increased permeability with depth were apparent. Based on this study, 1.3 mm injury depth was optimal since the hippocampus was still intact and vascular leak was maximal with this injury level at three days.

Figure 3:
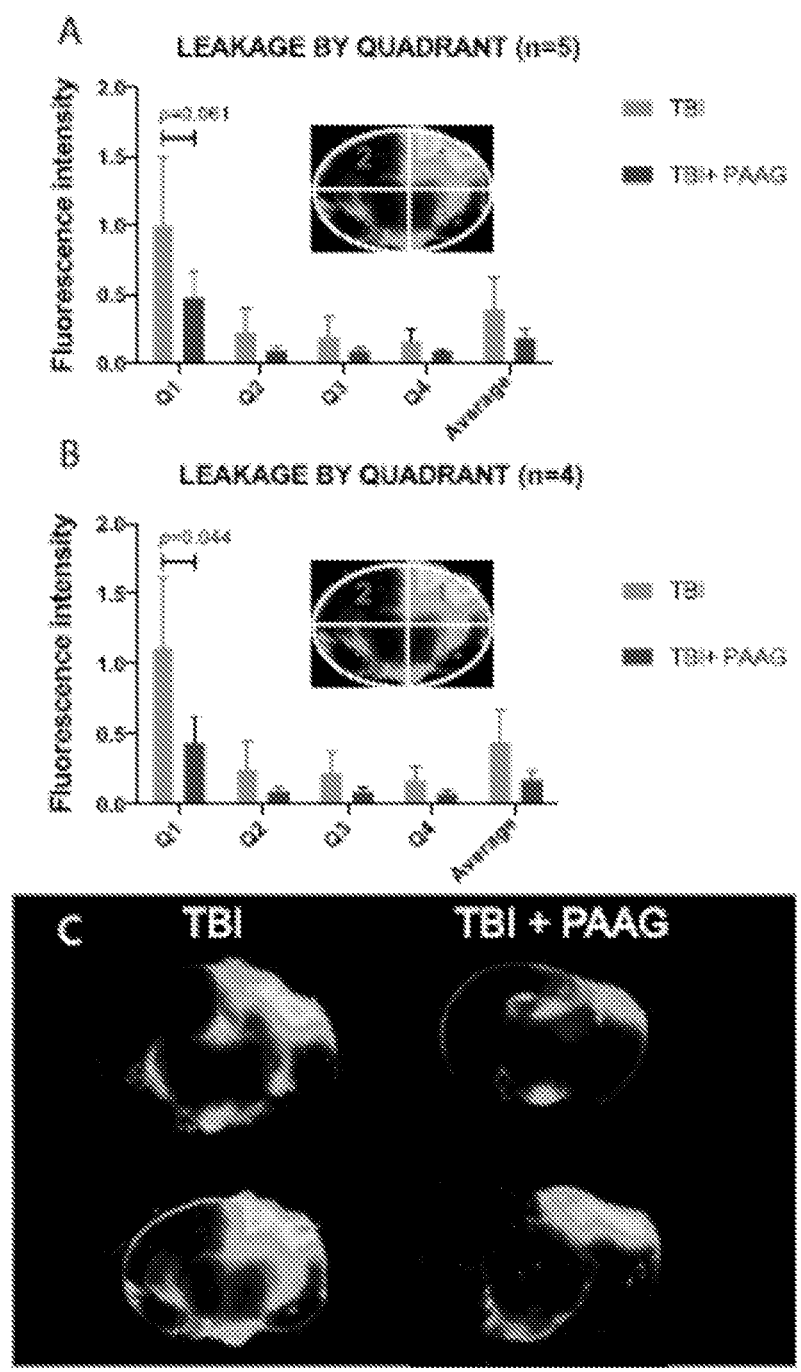
FIG. 3. Quantification of vascular leak for PAAG treated and control animals in full cohort FIG. 4. Quantification of vascular leak for PAAG treated and control animals.

The differences in the average fluorescence intensity of quadrant 1, where the injury was located approached significance (p=0.061) (TBI: 1+/−0.50, TBI+PAAG: 0.48+/−0.19) n=5 mice/group. Representative images of brain sections is shown in FIG. 3A. When two mice that proved difficult to inject were eliminated (one from each group), the results became significant (p<0.05) (TBI: 1.1+/−0.50, TBI+PAAG: 0.48+/−0.19). Representative images of brain sections of the experimental group with the non-conforming animals removed is shown in FIG. 3B. Exemplary images shown in FIG. 3C. N=4/arm mice/group PAAG reduced the amount of vascular permeability in an injured brain.

Example 3. Effects of PAAG on Blood Brain Barrier Permeability Induced by TBI Injury Depth 1.3 mm at 4.0 m/Sec Mice received 8 mg/kg PAAG or saline via tail vein at 1 hour after injury and four hours before sacrifice, which was three days after TBI. In addition, one hour before sacrifice, the mice received 200 ul of 1 mg/mL 10 kDa dextran conjugated with 680 Alexa Fluor-infrared dye. Mice were perfused with 60 mL ice cold PBS at a rate of 4 m/min via the left cardiac ventricle. The brain was then sectioned into 2 mm wide sections and scanned on a Li-Cor odyssey scanner (Li-Cor Bioscience, Inc.). Each section was divided into quadrants and the average fluorescence intensity calculated for each quadrant using Image Studio (Li-Cor Bioscience, Inc.). To quantitate the quadrant intensity for each brain, the average fluorescence intensity from three serial sections with the middle section containing the center of the injury site were averaged and normalized to Q1 of the control.

Figure 4:
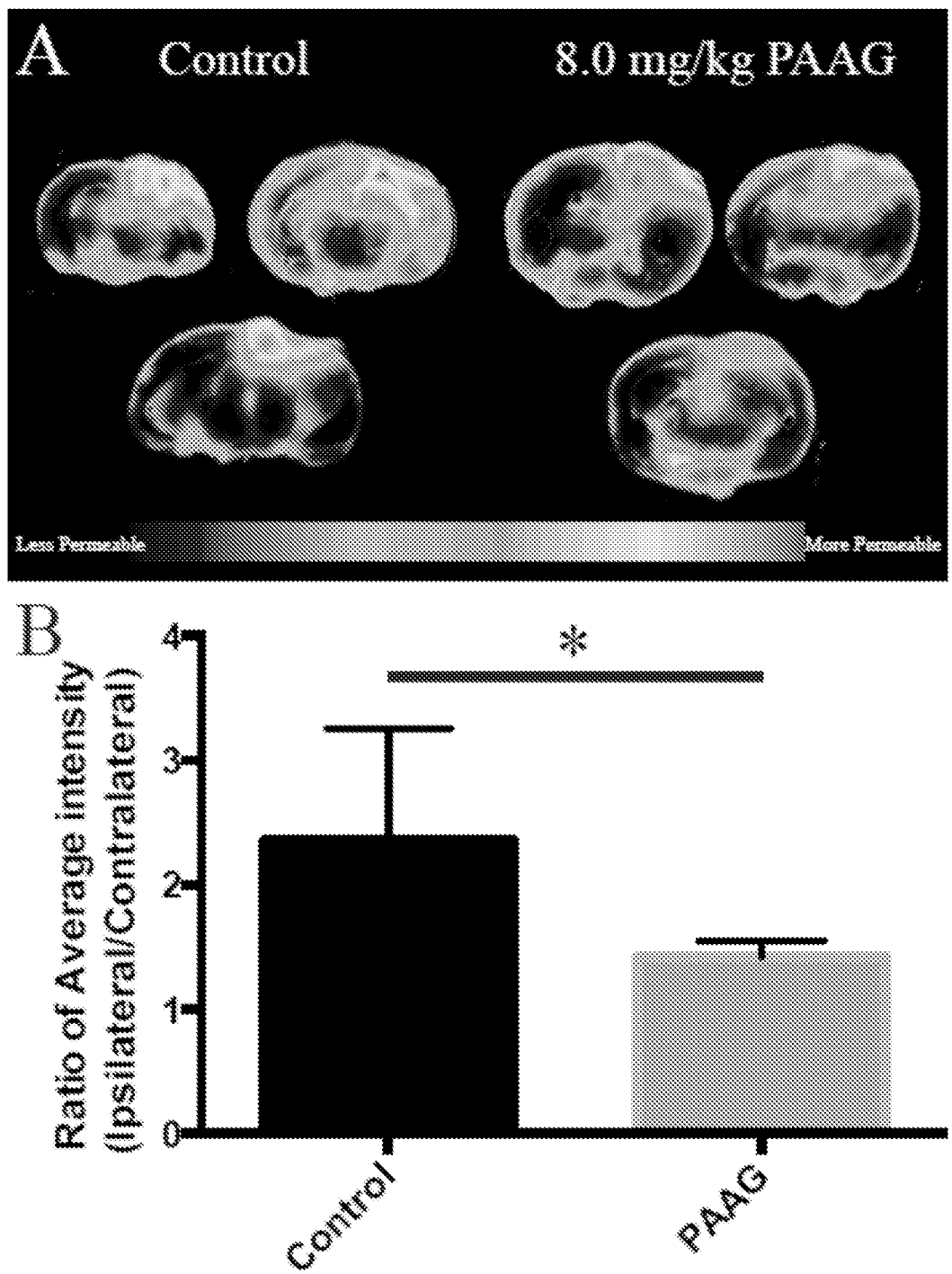

The differences in the average fluorescence intensity of quadrant 1, where the injury was located approached significance (p=0.061) (TBI+PAAG: 0.027) FIG. 4B. Exemplary images shown in FIG. 4A. The PAAG treated TBI mice demonstrated significantly decreased permeability to 10 kD IR tagged dye in the ipsilateral side of the brain. N=8 animals/group. P<0.027. 3 representational images of brain sections from each experimental group. N=4/arm mice/group.

Example 4. Effects of Intravenously Administered PAAG after Traumatic Brain Injury Each of two groups of eight animals were administered vehicle (control) or PAAG (experimental group). Both groups received an open skull traumatic brain injury via a controlled cortical impact (1.3 mm injury depth, 4.0 m/s). At 2 and 24 hours after injury, the animals received either 8 mg/kg PAAG (experimental group) or an equivalent volume of vehicle (control) via intravenous administration.

Three days after injury, the animals were sacrificed, then perfused with 30 ml of ice cold PBS, then 30 ml of 4% PFA in PBS through the left cardiac ventricle. After perfusion, the brains were left in 4% PFA overnight. The next day, they were transferred to 30% sucrose solution, and once they sank (2-3 days) they were placed in OCT and frozen using a platform chilled with dry ice.

The brains were then sectioned into 10 um thick sections, then stained. 8 sections across the injury site were stained, imaged and quantified.

Figure 5:
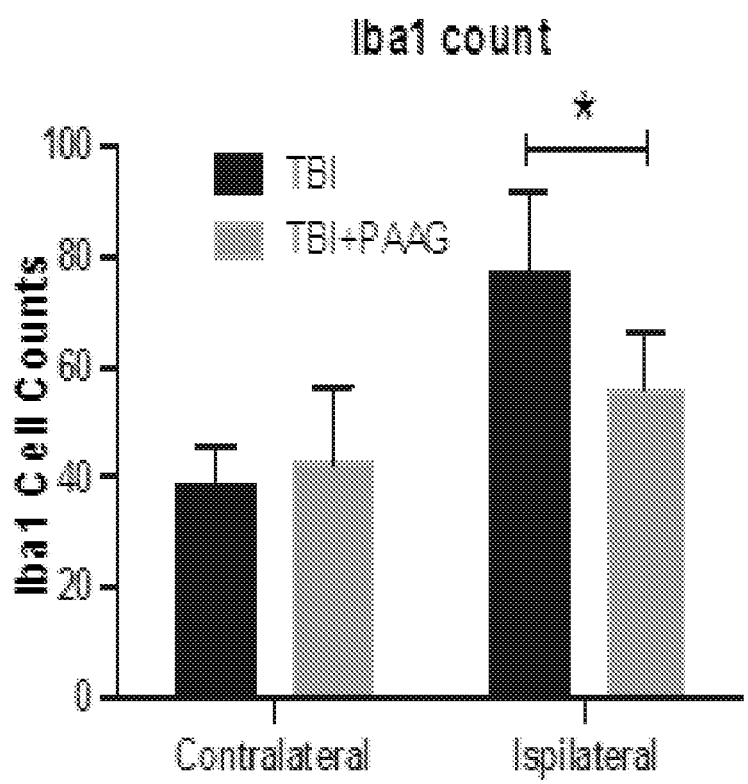
FIG. 5. Exemplary depiction of Iba1 cell counts for vehicle and PAAG-treated TBI animals.

Microglia activated by inflammation upregulated Iba1, as indicated in FIG. 5. When treated with PAAG, activation of microglia by inflammation was reduced.

Figure 6:
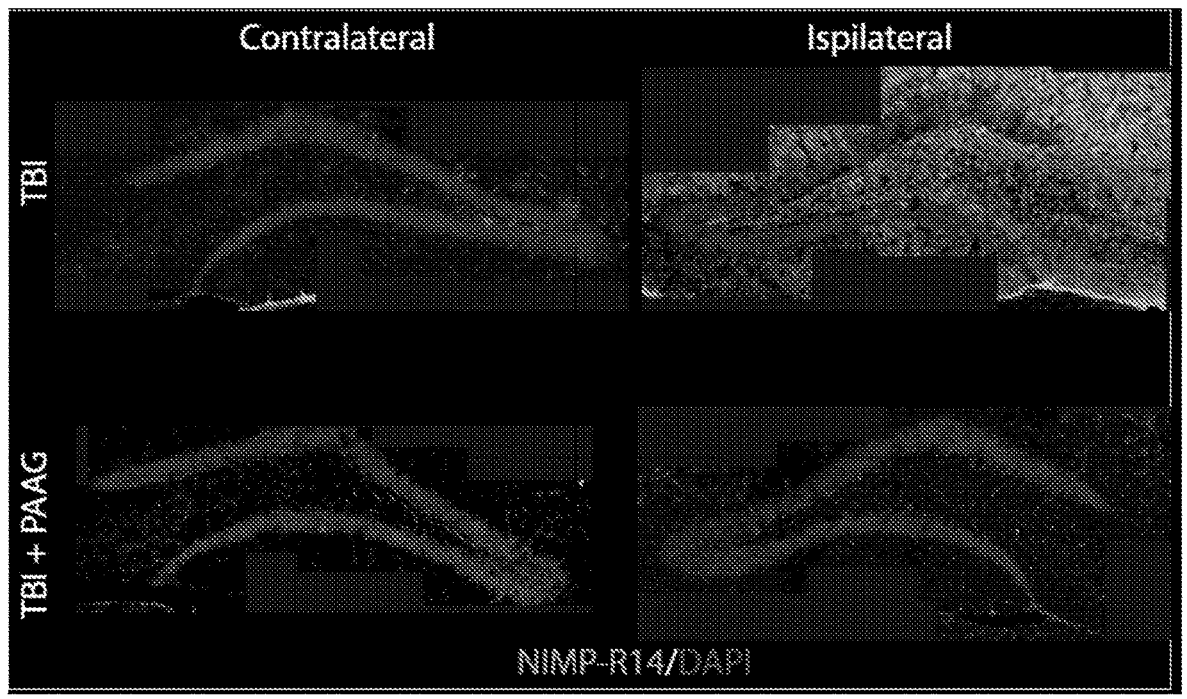
FIG. 6, Exemplary depiction of neutrophil infiltration as read by NIMPR-14 staining in PAAG-treated TBI animals.

As shown in FIG. 6, PAAG-treated animals also inhibited neutrophil infiltration as read by NIMPR-14 staining (n=3).

Example 5. Hemorrhagic Shock Study in Rats

Fourteen male Sprague-Dawley rats breathing spontaneously 100% $O_2$ were anesthetized with isoflurane (2%) and tracheostomized. The carotid artery was cannulated for recording blood pressure. Femoral vein and artery were cannulated for fluorescent dyes infusion and blood withdrawal (hemorrhage and blood samples), respectively. Hemorrhagic Shock (HS)/resuscitation treatment as either a combination of PAAG (8 mg/kg)+LR (15 ml/kg, low volume) or LR alone (45 ml/kg). Unshocked animals (baseline) and post resuscitation animals (Lactated Ringers solution (LR) or PAAG+LR) were compared.

A microscope with an immersion objective (Zeiss 63×, N.A. 0.95) and filter sets for Texas Red (TR) and fluorescein isothiocyanate (FITC) fluorescence was used, connected to a velocity measuring device (Optical Doppler Velocimeter) and to a digital camera (CoolSnap CF). The cremaster muscle was positioned over a thermostatically-controlled pedestal and covered with an impermeable plastic film.

Dextrans (70 and 500 kDa) labeled with TR or FITC were used to measure the space occupied by the glycocalyx (5, 6). At baseline, TR-Dextran 70 (10 mg/ml) was injected for determining the intact glycocalyx thickness, followed by FITC-Dextran 500 (10 mg/ml) after HS/resuscitation.

The endothelial glycocalyx thickness was measured as follows. Briefly, epi- and trans-illumination images were used to measure the fluorescent column width and the microvessel anatomical (lumen) diameter. The glycocalyx thickness was estimated by the difference between these two measurements.

Figure 7:
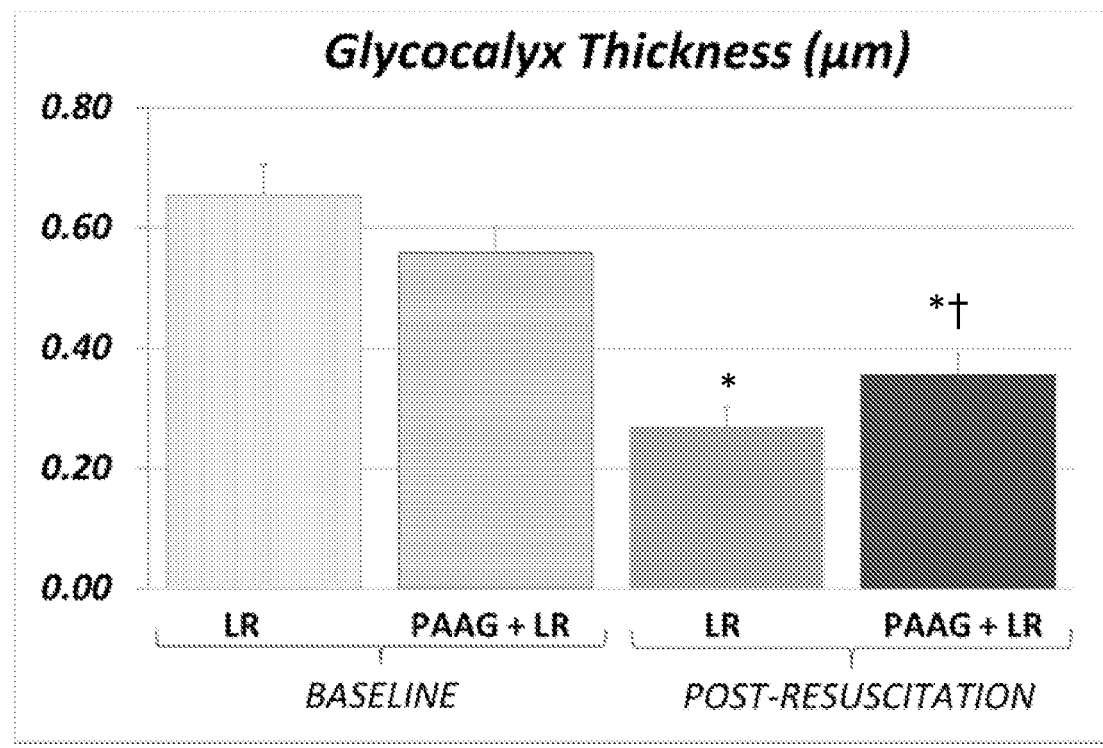
FIG. 7. Exemplary depiction of glycocalyx thickness for animals unshocked and post resuscitation.

FIG. 7 depicts the glycocalyx thickness for animals unshocked and post resuscitation. Endothelial glycocalyx thickness (top) measured in post-capillary venules from cremaster muscle of rats subjected to shock followed by resuscitation with PAAG+LR (n=20 vessels) or LR alone (n=30 vessels). EG shedding was significantly higher at post-resuscitation with LR alone compared to baseline and PAAG+LR. Data was expressed as mean±SEM. * Significantly different from baseline (p<0.05); † Significantly different from LR alone (p<0.05).

Figure 8:
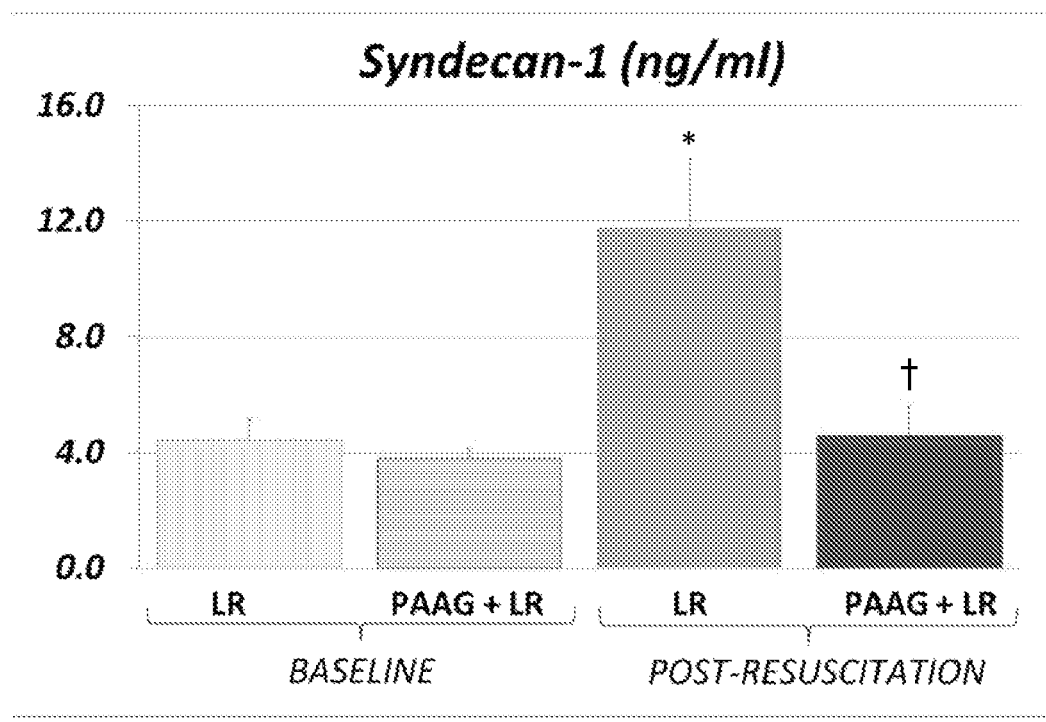
FIG. 8. Exemplary depiction of plasma Syndecan-1 proteoglycan before and after HS/resuscitation.

FIG. 8 depicts levels of plasma Syndecan-1 proteoglycan before and after HS/resuscitation with PAAG+LR (N=4 experiments/group) or LR alone (N=7 experiments/group). Post-resuscitation levels of Syndecan-1 in PAAG group did not change compared to baseline levels, and were significantly lower than those in LR alone group. Data expressed as mean±SEM. * Significantly different from baseline (p<0.05); † Significantly different from LR alone (p<0.05).

The invention claimed is:

1. A method of treating hemorrhagic shock in a subject in need thereof, the method comprising intravenously administering an effective amount of a polymer to the subject, thereby treating the hemorrhagic shock, wherein the polymer is a compound of the following structure:

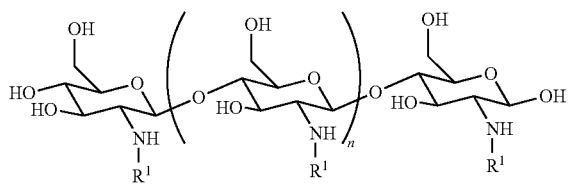

wherein:
n is an integer between 20 and 6000; and
each R¹ is independently selected for each occurrence from hydroaen, acetyl,

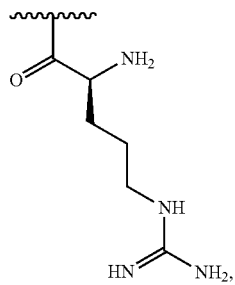    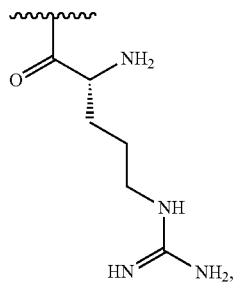

wherein at least 25% of R¹ substituents are H, at least 1% of R¹ substituents are
acetyl, and at least 2% of R¹ substituents are

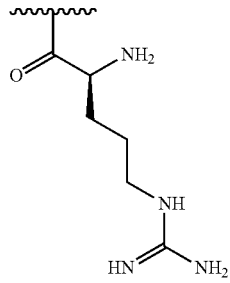   or   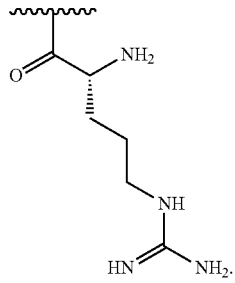

2. The method of claim 1, wherein the method restores normal blood transport or reduces abnormal fluid transport in the subject.

3. The method of claim 1, wherein the method reduces the permeability of the blood brain barrier.

4. The method of claim 1, wherein the method enhances the integrity of the blood brain barrier.

5. The method of claim 1, wherein the hemorrhagic shock is a result of dysfunction of the glycocalyx or loss of structural integrity of the glycocalyx.

6. The method of claim 1, wherein the method reduces VEGF-mediated deterioration.

7. The method of claim 1, wherein the polymer is soluble at physiologic pH.

8. The method of claim 1, wherein the polymer has a molecular weight (MW) between 30 and 300 kDa.

9. The method of claim 1, wherein the polymer is 10-35% functionalized.

10. The method of claim 1, wherein the polymer interacts with the glycocalyx surface.

11. The method of claim 1, wherein the polymer is a charged polymer.

12. The method of claim 1, wherein the charged polymer is a polycationic polymer.

13. The method of claim 1, wherein the intravenous administration is by bolus administration.

14. The method of claim 1, wherein the intravenous administration is by continuous infusion.

15. The method of claim 1, wherein the administration is intraarterial.

16. The method of claim 1, wherein the polymer has a polydispersity index of about 1.0 to about 2.5.

* * * * *

UNITED STATES PATENT AND TRADEMARK OFFICE
CERTIFICATE OF CORRECTION

PATENT NO. : 11,911,412 B2
APPLICATION NO. : 17/362254
DATED : February 27, 2024
INVENTOR(S) : Shenda Baker et al.

Page 1 of 1

It is certified that error appears in the above-identified patent and that said Letters Patent is hereby corrected as shown below:

In the Claims

At Column 21, Claim 1, Line 13, replace "from hydroaen, acetyl," with -- from hydrogen, acetyl, --.

Signed and Sealed this
Thirtieth Day of April, 2024

*Katherine Kelly Vidal*

Katherine Kelly Vidal
*Director of the United States Patent and Trademark Office*